United States Patent
Hughes et al.

(10) Patent No.: US 8,792,960 B2
(45) Date of Patent: Jul. 29, 2014

(54) MAGNETIC RESONANCE METHOD AND APPARATUS FOR AUTOMATED ANALYSIS OF JOINT INFLAMMATION, JOINT PROTEOGLYCAN PROPORTION, AND JOINT OSTEOARTHRITIS

(75) Inventors: Timothy Hughes, Erlangen (DE); Tallal Charles Mamisch, Zurich (CH)

(73) Assignees: Siemens Aktiengesellschaft, Munich (DE); Inselspital-Stiftung, Bern (CH)

( * ) Notice: Subject to any disclaimer, the term of this patent is extended or adjusted under 35 U.S.C. 154(b) by 694 days.

(21) Appl. No.: 12/710,869

(22) Filed: Feb. 23, 2010

(65) Prior Publication Data

US 2010/0217110 A1    Aug. 26, 2010

(30) Foreign Application Priority Data

Feb. 23, 2009   (DE) .......................... 10 2009 010 175

(51) Int. Cl.
| | |
|---|---|
| *A61B 5/055* | (2006.01) |
| *A61K 49/06* | (2006.01) |
| *G01R 33/56* | (2006.01) |
| *G01R 33/20* | (2006.01) |

(52) U.S. Cl.
CPC ............. *A61B 5/055* (2013.01); *A61K 49/06* (2013.01); *G01R 33/5601* (2013.01); *G01R 33/20* (2013.01)
USPC ........................................ 600/410; 600/407

(58) Field of Classification Search
USPC .................................. 600/407–435
See application file for complete search history.

(56) References Cited

U.S. PATENT DOCUMENTS

2007/0015995 A1*   1/2007   Lang et al. .................. 600/407

OTHER PUBLICATIONS

"Spatial Assessment of Articular Cartilage Proteoglcans With Gd-DTPA-Enhanced T1 Imaging." Nieminen et al. Magnet Resonance in Medicine (2002) vol. 48. pp. 640-648.*

(Continued)

*Primary Examiner* — Tse Chen
*Assistant Examiner* — Mark Remaly
(74) *Attorney, Agent, or Firm* — Schiff Hardin LLP

(57) ABSTRACT

In a magnetic resonance method and apparatus for generating an analysis of an inflammation of a joint, for determining a proteoglycan proportion of a joint, and for generating an analysis of osteoarthritis of a joint, for a predetermined region within a body of a patient, a three-dimensional MR image data set is generated with a magnetic resonance imaging scanner. At least, a portion of a joint is located within the region. For each of several different automatically determined layers, a two-dimensional MR image is calculated from the three-dimensional MR image data set. For each layer, the thickness of a predetermined tissue, which is represented in the two-dimensional MR image corresponding to the layer, is determined, by means of which an analysis of a joint inflammation is automatically determined depending on the respective thicknesses. A further layer in the region is also automatically determined and, after injecting a contrast medium, a two-dimensional T1-weighted MR image is generated for this layer, from which a proteoglycan proportion is automatically determined. From the analysis of the joint inflammation and the proteoglycan proportion, it is then possible to perform a reproducible analysis of osteoarthritis of the joint.

11 Claims, 2 Drawing Sheets

(56) References Cited

OTHER PUBLICATIONS

"A Non-invasive Technique for 3 Dimensional Assessment of Articular Cartilage Thickness Based on MRI Part 1: Development of a Computational Method", A. Lösch et al.; IN: Magnetic Resonance Imaging (1997), vol. 15, No. 7, pp. 795-804.

"Determination of 3D Cartilage Thickness Data From MR Imaging: Computational Method and Reproducibility in the Living", Stammberger et al., IN: Magnetic Resonance in Medicine (1999), vol. 41(3), pp. 529-536.

"PA57: Spatial MRI Assessment of Articular Cartilage Proteoglycans in Vivo", Nieminen et al., IN: Osteoarthritis and cartilage, Bailliere Tindal, London, GB, (2001) vol. 9, pp. S37-S38.

"On-line Automatic Slice Positioning for Brain MR Imaging", van der Kouwe et al., IN: Neuroimage (2005), vol. 27, No. 1, pp. 222-230.

"Pharmacokineic MR Analysis of the Cartilage is Influenced by Field Strength", Marti-Bonmati et al., IN: European Journal of Radiology, (2008), vol. 67, No. 3, pp. 448-452.

\* cited by examiner

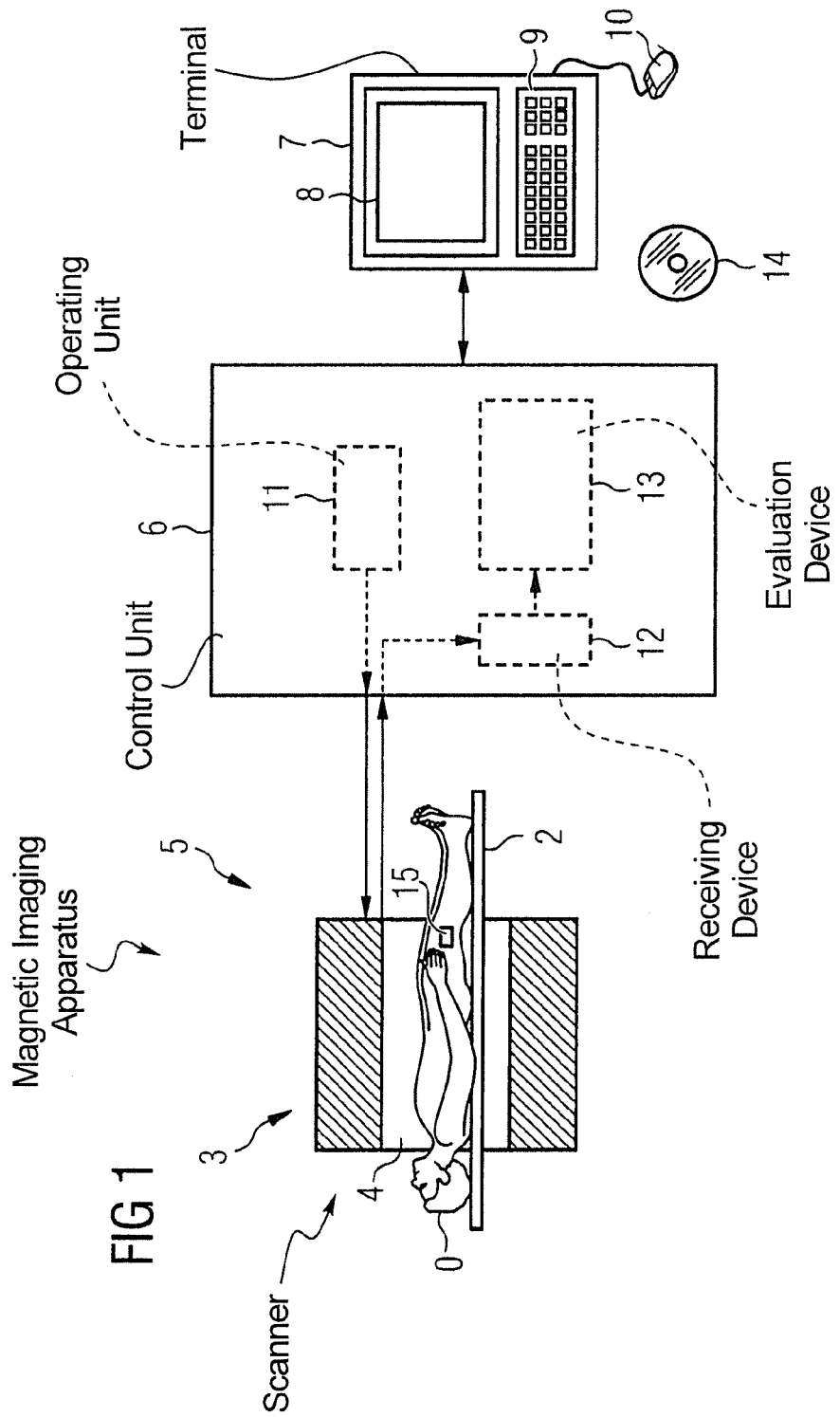

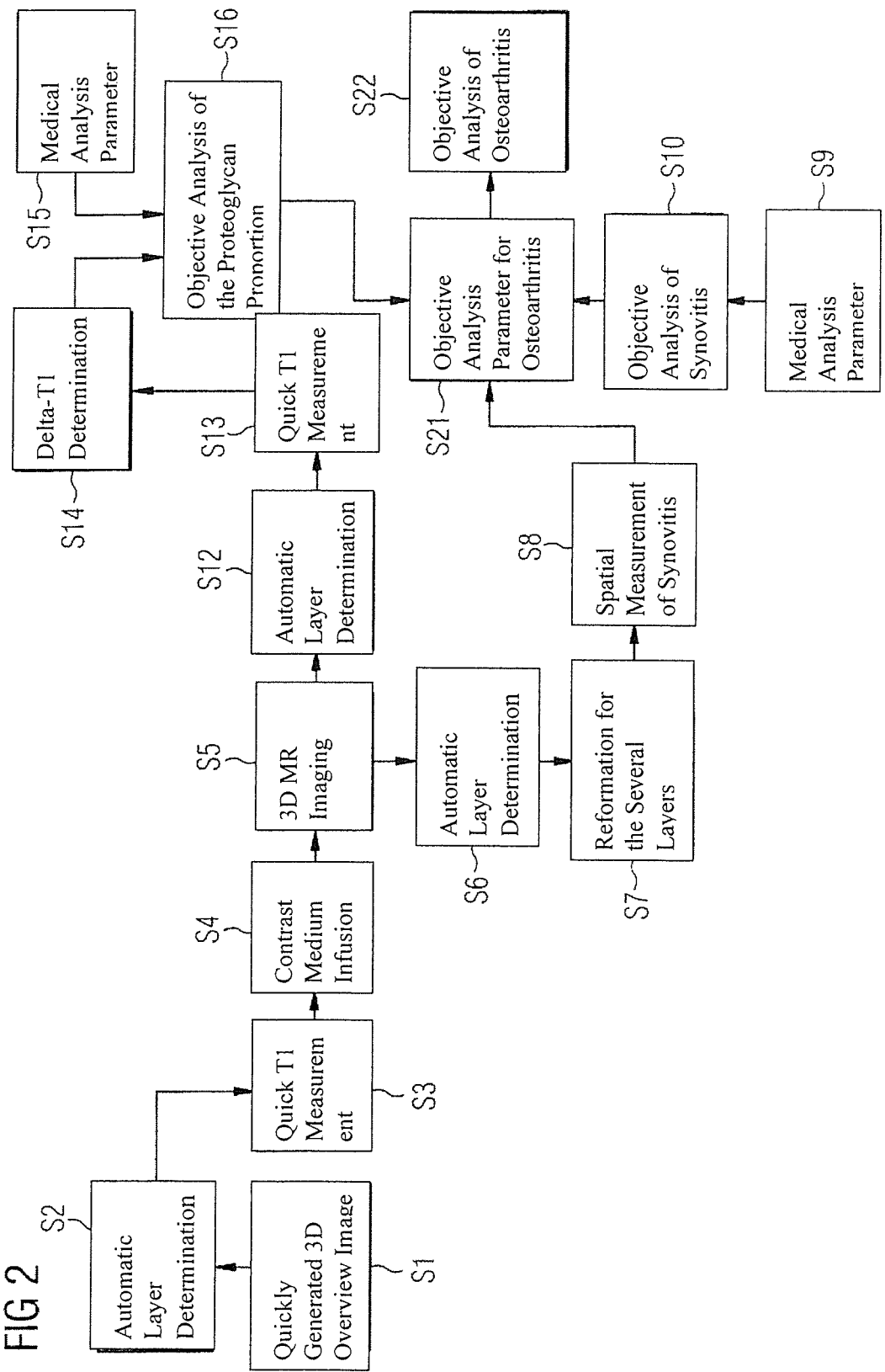

MAGNETIC RESONANCE METHOD AND APPARATUS FOR AUTOMATED ANALYSIS OF JOINT INFLAMMATION, JOINT PROTEOGLYCAN PROPORTION, AND JOINT OSTEOARTHRITIS

BACKGROUND OF THE INVENTION

1. Field of the Invention

The present invention concerns magnetic resonance methods and devices for analyzing a joint inflammation, for determining a proteoglycan proportion in the region of the joint, and/or for analyzing osteoarthritis.

2. Description of the Prior Art

Osteoarthritis (OA) is a process of joint deterioration encompassing of various factors and involves the loss of functional capability of the joint. It is not yet possible to perform a reproducible classification or analysis of osteoarthritis that measures the damage of the cartilage and other joint structures (including the synovial fluid). Techniques are indeed known to determine and to quantify a degree of inflammation of the synovial fluid and a degeneration of the respective cartilage structures, but these techniques are not able to supply reproducible results. For example, it is not yet possible to provide such reproducible analysis or quantification of osteoarthritis in an MR imaging procedure.

According to prior art, the following techniques are used for the purpose of analyzing osteoarthritis:

Two-dimensional MR measurements are used to determine the thickness of a layer of tissue damaged by synovitis. In the process, the thickness of the tissue damaged by synovitis is determined manually by a physician performing several MR measurements at different sections of the respective joint and manually measuring the thickness of the layer of tissue damaged. Thus it is almost impossible to reproduce the results since even the same physician in examining his or her results would have difficulties to repeat the MR measurements at the same sections of the joint.

Moreover, it is known to perform a T1 measurement in a specific region of the joint after administering a T1 contrast medium. By means of such a T1 measurement the proteoglycan proportion in the region of the joint is measured that, in turn, is a measured value of the degeneration within the joint. This known determination of the proteoglycan proportion involves the following problems:

It takes at least 30 minutes until an adequate amount of T1 contrast medium has been absorbed in the region of the joint, which results in a respective waiting period for the patient.

In order to guarantee reproducibility it would be important to also perform a T1 measurement before administering the T1 contrast medium. Because of the above-mentioned period of waiting until an adequate amount of T1 contrast medium has been absorbed in the region of the joint, the patient has to be placed twice in a respective magnetic resonance imaging scanner, which is cumbersome, time-consuming and therefore expensive. What is more, it is extremely difficult for the same physician to perform the two T1 measurements before and after administering the T1 contrast medium, if a manual process is used to measure the same region of the joint.

In order to be able to compare subsequent measurements it is important that the T1 measurement is performed in the same region of the joint, which is almost impossible to do if the process is performed manually.

A further problem involves the feeding of the information obtained through the T1 measurement(s) consistently and reproducibly into a rating system.

According to prior art, there exists the further possibility of using a process in which a respective image of the joint is produced by means of a morphologic MR process, and respective tissue alterations of the joint and respective alterations of the associated structures within the joint (for example, the meniscus, ligaments or bones) are analyzed in order to generate an analysis of the osteoarthritis.

In summary the known procedures of analyzing osteoarthritis art are not ideal for providing reproducible results because they are cumbersome and have limited properties.

SUMMARY OF THE INVENTION

An object of the present invention is to alleviate the above-mentioned disadvantages associated with such known procedures, in order to provide improved processes and devices for the purpose of generating an analysis of osteoarthritis.

This object is achieved in accordance with the present invention, by a method to automatically generate an analysis of inflammation or synovitis of a joint using a magnetic resonance imaging scanner. The method includes the following steps.

A three-dimensional MR image data set of a predetermined region within a body is generated by means of the magnetic resonance imaging scanner. The predetermined region includes at least apportion of the joint to be examined. Preferably, a complete three-dimensional data set of the joint to be examined is generated in this step.

The position or orientation for different layers within the predetermined region is determined. In this step, the preset parameters precisely define the different layers so that any subsequent process or a repetition of the procedure operates with exactly the same layers if it is performed with the same preset parameters.

For each of the different layers, a two-dimensional MR image is automatically reconstructed from the three-dimensional MR image set. Thus a magnetic resonance imagining scanner is not required for this step, because the two-dimensional MR images for the different layers are only calculated through a type of re-formatting of the available three-dimensional MR image data set.

For each layer, a thickness of the predetermined tissue, which is available in the two-dimensional MR image corresponding to the layer, is determined by means of the two-dimensional MR image calculated for this particular layer. In particular, the predetermined tissue comprises an internal joint membrane damaged by synovitis. The measurement of the thickness and thus the determination of the extent to which the tissue has been damaged by synovitis can be made manually of automatically.

Finally, depending on the determined or measured thickness of the predetermined tissue, an analysis of the joint inflammation is derived and made available in a humanly perceptible form.

By predetermining in reproducible fashion the position of the different layers, or automatically determining that position within the three-dimensional MR image data set (by means of which the layers are determined distinctly as well as reproducibly), and by the automatic calculation of the two-dimensional MR images for these particular layers from the three-dimensional MR image data set, it is possible to provide a reproducible determination of the thickness of the internal joint membrane, and thus a reproducible analysis of an inflammation of the joint or osteoarthritis.

The predetermination of the positions of the different layers can also be performed by automatically determining the positions for each layer. For this purpose, a determination of the different layers and thus a determination of the position of the different layers is performed, for example, automatically by means of a predetermined anatomical orientation point (for example, a meniscus or a ligament), which is being localized in the three-dimensional MR image data set. Based on this anatomical orientation point (anatomical landmark), it is possible to determine the position of the joint and hence the position of the layers within the three-dimensional MR image data set. In this context, the term "orientation point" should not be viewed as a "point" but rather as an orientation guide for the purpose of determining the layers. If the predetermined orientation point or orientation guide is a meniscus, the inventive process localizes, for example, a meniscus by means of pattern recognition within the three-dimensional MR image data set and determines, for example, from the position of the meniscus the position of the whole knee joint and thus the position of the different layers.

By determining the layers by means of an anatomical orientation point (landmark), the determination of the layers is performed automatically for the first, as well as for any following analysis of the joint inflammation, which further improves the reproducibility of the results.

In an embodiment, the determination of the thickness of the tissue (in particular the thickness of the internal joint membrane damaged by synovitis) is performed automatically by automatically localizing the respective tissue in the two-dimensional MR image and automatically measuring the thickness of the tissue.

Measuring the thickness of the tissue automatically further improves the reproducibility of the analysis of the joint inflammation since with a comparable data basis an automatic process always produces the same results in comparison to a human.

The present invention also encompasses a method for automatic determination of a proteoglycan proportion of a joint using a magnetic resonance imaging scanner. This method includes the following steps.

By means of a preset parameter for the position or orientation of a layer, the layer is automatically determined in a region of the joint to be examined.

After injecting a T1 contrast medium (for example, a contrast medium based on gadolinium that is administered by infusion), a two-dimensional T1-weighted MR image is generated for the layer, and T1 times are determined.

Depending on the two-dimensional MR image (in particular depending on the T1 times determined), the proteoglycan proportion in the joint is determined.

Automatically determining the layer for which the T1 measurement has been performed by means of a preset parameter has the advantage that the reproducibility of determining the proteoglycan proportion can be guaranteed because, by the automatic determination it is possible to also determine the same layer in subsequent measurements. The parameter for the position of the layer can be set, for example, by means of spatial coordinates and directional vectors that correspond to an orientation point of the joint. In this way, the position of the layer within the region can be clearly defined. At the same time, as described above, such an orientation point can be automatically recorded.

In a preferred embodiment of the invention, a two-dimensional T1-weighted original MR image is generated for the automatically determined layer prior to injecting the T1 contrast medium. In this way, it is possible to generate a difference between the two-dimensional T1-weighted MR image and the two-dimensional T1-weighted original MR image. Depending on these differences, in particular depending on differences between T1 times from the T1-weighted MR image and T1 times from the T1-weighted original MR image, it is then possible to determine the proteoglycan proportion more precisely and reproducibly.

In a further embodiment of the invention, the position of the layer is determined by means of a previously generated three-dimensional image data set overview (low resolution). For example, in the image data set overview, a specific pattern or orientation point of the joint is localized and the position of the layer is determined in reference to this pattern or point. Advantageously, this results in the fact that this same layer can be used to generate automatically the T1-weighted MR image, as well as to generate automatically the T1-weighted original MR image. Thus it can be guaranteed that the T1 measurements originate from the same anatomical region of the joint, which increases the validity of the T1 differences and allows for subsequent measurements, for example, of the T1 times, to be reproduced.

Consequently, it is possible to determine the proteoglycan proportion by the T1 times in the one and same layer being determined before as well as after an injection of the T1 contrast medium has been administered, and by the proteoglycan proportion being determined depending on the difference between the T1 times after the injection and the T1 times before the injection.

By differentiating the T1 times by means of T1-weighted original MR images, it is possible to determine the concentration of the contrast medium in cartilage, and thus the proteoglycan proportion in the cartilage or joint, even when it involves different types of cartilage, including surgically restored cartilage tissue.

According to the invention, instead of using the overview image (with low resolution), it is also possible to generate and use a three-dimensional MR image data set (with high resolution) in order to determine therein automatically the respective layer, which is used as a basis for generating the T1-weighted MR image after the injection and performing the T1 measurement.

The present invention also encompasses a method for automatically generating an analysis of osteoarthritis of a joint by the use of a magnetic resonance imaging scanner. According to this method, the scanner performs the previously described method for automatically generating an analysis of a joint inflammation, as well as the inventive process for automatically determining a proteoglycan proportion of a joint. The analysis of the joint inflammation and the proteoglycan proportion are used as a basis for analyzing the osteoarthritis.

Thus, the inventive method for analyzing osteoarthritis combines two biomarkers into an overlapping medical and objective analysis of osteoarthritis. This, in turn, improves the validity and precision in comparison to an analysis based on merely one biomarker.

In the method, the T1 contrast medium in particular is administered before generating the three-dimensional MR image data set.

Since the generation of the three-dimensional MR image data set normally represents the longest phase of the inventive method for analyzing the osteoarthritis, this time can be used for the previously administered T1 contrast medium to spread in the joint to be examined. In this way, it is possible to achieve an almost optimum interaction or combination of the processes of analyzing a joint inflammation or of determining the proteoglycan proportion.

The present invention also encompasses a control device for operating a magnetic resonance imaging scanner to generate an analysis of a joint inflammation. The device includes an operating unit that operates the magnetic resonance imaging scanner, a receiving device to receive MR data of a predetermined region within the body of a patient that have been acquired by the magnetic resonance imaging scanner, and an evaluation device to analyze the received MR data. The predetermined region includes at least a portion of the joint to be examined. The operating unit operates the magnetic resonance imaging scanner so that the magnetic resonance imaging scanner generates a three-dimensional MR image data set with high resolution of the region. Depending on a preset parameter, the evaluation device determines then a position for different layers within the predetermined region. For each of the layers, the evaluation device calculates a two-dimensional MR image from the previously generated three-dimensional MR image data set. By means of each of these two-dimensional MR images, the evaluation device determines a thickness of a predetermined tissue (in particular an internal joint membrane damaged by synovitis), which is represented in the two-dimensional MR image corresponding to the respective layer. Depending on the thicknesses thus determined, the evaluation device generates an analysis of the joint inflammation of the respective joint.

Basically, the advantages of the device according to the invention correspond to the advantages of the process of automatically generating an analysis of a joint inflammation, which has previously been described in detail. Therefore, it is not necessary to repeat these details.

Moreover, the present invention also encompasses a control device for operating a magnetic resonance imaging scanner to determine a proteoglycan proportion of a joint. This device has an operating unit that operates the magnetic resonance imaging scanner, a receiving device to receive MR data of a predetermined region within the body of a patient acquired by the magnetic resonance imaging scanner, and an evaluation device to analyze the received MR data. Depending on a preset parameter for the position of a layer, the evaluation device determines in the predetermined region the layer corresponding to the position. Subsequently, the operating unit operates the magnetic resonance imaging scanner, after an injection of a T1 contrast medium has been administered, to generate a two-dimensional T1-weighted MR image for the respective layer. Depending on the two-dimensional T1-weighted MR image that is generated, from which MR image especially the T1 times can be derived, the evaluation device then determines the proteoglycan proportion of the joint.

The device according to the invention is designed to generate a three-dimensional image data set overview (low resolution) for the predetermined region of the joint, using the image data set overview to determine the position or orientation of the joint and thus the position of the layer in which the two-dimensional T1-weighted MR image is being generated. The device operates the scanner to generate the two-dimensional T1-weighted MR image before the injection in the same layer as the two-dimensional T1-weighted MR image after the injection. This results in the advantage that the device can acquire the T1 times in the same layer before and after the injection in order to determine the proteoglycan proportion of the joint depending on the difference of these T1 times.

The device to generate an analysis of a joint inflammation embodies the advantages described above with regard to the corresponding method The present invention also encompasses a control device for operating a magnetic resonance imaging scanner to generate an analysis of osteoarthritis of a joint. This inventive device also has an operating unit that operates the magnetic resonance imaging scanner, a receiving device to receive MR data of a predetermined region within the body of a patient acquired by the magnetic resonance imaging scanner, and an evaluation device to analyze the received MR data. The predetermined region includes at least a portion of the joint to be examined, as well as a device to determine a proteoglycan proportion of the joint. In other words, the inventive device for analyzing osteoarthritis is designed on the same basis as the previously described inventive device for generating an analysis of a joint inflammation. The inventive device determines an analysis of osteoarthritis of the joint by a combination of analysis of joint inflammation and the proteoglycan proportion of the joint.

Basically, the advantages of the inventive device correspond to the advantages of the inventive method for generating an analysis of osteoarthritis of a joint that have been previously described in detail. Therefore, repetition of those advantages is not necessary.

Furthermore, the present invention encompasses a magnetic resonance imaging apparatus having a scanner and either of the inventive devices described above.

The present invention also encompasses a computer-readable, non-transitory (tangible) data carrier (medium), for example, a DVD, a magnetic tape or a USB stick which stores electronically readable control information, i.e., programming information. When the data carrier is loaded into a control or processing unit of a magnetic resonance imaging apparatus, all of the inventive embodiments of the methods described above can be performed. The programming instructions include, for example, libraries and auxiliary functions in order to realize the respective embodiments of the methods. The programming instructions can be a source code (for example in C++) that must be still compiled and linked, or that must be only interpreted, or a workable software code that, for implementation, must only be loaded into the respective processing unit.

Although, the present invention can be used to analyze osteoarthritis, it is not restricted to this preferred field of application, because the present invention can also be used to generate a two-dimensional MR image that can be used for the purpose of comparing one and the same layer or one and the same layer position at time intervals of approximately one year.

BRIEF DESCRIPTION OF THE DRAWINGS

FIG. 1 schematically illustrates a magnetic resonance imaging scanner with a control unit according to the invention.

FIG. 2 is a flowchart of an inventive process that generates an analysis of osteoarthritis depending on an analysis of a joint inflammation and depending on a proteoglycan proportion of the joint.

DESCRIPTION OF THE PREFERRED EMBODIMENTS

FIG. 1 shows an inventive magnetic resonance imaging apparatus 5. Basically, the magnetic resonance imaging apparatus 5 includes a scanner 3 that generates, in an examination region 4, the magnetic field required for the MR examination, a table 2, a control unit 6 that controls the scanner 3 and records MR data from the scanner 3, and a terminal 7 connected to the control unit 6.

The control unit 6, in turn, includes an operating unit (controller or sequencer) 11, a receiving device 12 and an evaluation device 13. During an MR examination, MR data are acquired from the receiving device 12 by means of the scanner 3. In the process, the operating unit 11 controls the scanner 3 to acquire MR data acquired from a volume 15 inside the body of a patient O lying on the table 2.

The evaluation device 13 processes the MR data so as to be presented graphically on the monitor 8 of the terminal 7 with the analyses generated according to the invention being included in the graphics display. In addition to the graphical representation of MR data, it is possible with the terminal 7, which includes besides the monitor 8 a keyboard 9 and a mouse 10, for a user to predetermine the position of a layer or medical evaluation parameter and further preset parameters in order to perform the inventive process. By means of the terminal 7, it is also possible to load the operating software according to the invention into the control unit 6, particularly into the evaluation device 13. The software of the control unit 6 can embody one or several of the inventive processes and can be also stored on a DVD 14. The software can be read by the terminal 7 from the DVD 14 and can be copied into the control unit 6.

FIG. 2 shows a flowchart of an inventive process for objectively analyzing osteoarthritis.

In a first method step S1, a three-dimensional overview image with low resolution of a region within the body of a patient is generated within a short period of time (less than 5 min.). This region includes at least a portion of a joint to be examined.

In the next step S2, based on this three-dimensional overview image, a layer is automatically determined. For this purpose, for example, by means of pattern recognition algorithms, a particularly distinctive characteristic or pattern of the joint can be recorded in the three-dimensional overview image, making it possible to determine a position of the joint. In relation to the position, an ideal layer for recording a proteoglycan proportion of the joint is then automatically determined.

In the next step S3, using the magnetic resonance imaging apparatus 5, a quick T1 scan is performed for the layer thus determined.

Subsequently, in step S4, the patient receives an infusion of a T1 contrast medium. Administering the T1 contrast medium in the form of an infusion instead of in the form of a tablet has the advantage that the contrast medium remains for a longer period at the interface between the joint and the surrounding tissue, resulting in a higher diffusion rate in the cartilage.

In step S5, after or during the period of infusing the contrast medium, a three-dimensional MR image data set with high resolution (higher than with the overview image of S1) is generated from the predetermined region and thus from the joint.

In the next step S6, several layers for measuring the thickness of a tissue damaged by synovitis are automatically determined. This automatic layer determination S6 can be performed according to the same principles as the automatic layer determination in S2, so that, even in step S6, the layers are determined automatically (without manual interference) in relation to the position of the joint to be examined.

In step S7, for each of the layers determined in step S6, two-dimensional MR images are calculated from the three-dimensional MR image data set which was generated in step S5. In other words, step S7 is performed exclusively on a data processor, for example, on the evaluation device 13 or the computer 7, in that the two-dimensional MR images are calculated by reformatting the data included in the three-dimensional MR image data set, or by bringing said data into a new or converted format.

Based on the two-dimensional MR images calculated in step S7, the tissue damaged by synovitis is now measured in step S8. For example, by means of pattern recognition algorithms, the tissue damaged by synovitis (mostly the internal joint membrane) is recorded and measurements (in particular thickness) of the respective tissue layer are determined.

The measurements performed in step S8 are then analyzed on the basis of specific evaluation parameters which the respective physician can preset in step S9. In this way, it is possible to generate an objective and reproducible analysis of the synovitis of the respective joint.

Based on the three-dimensional MR image data set generated in step S5, an automatic layer determination is performed in step S12, in which the same layer is determined as in step S2. It would, of course, also be possible to perform the automatic layer determination in S12 by means of a three-dimensional overview image, as is the case in the automatic layer determination in S2. However, since the three-dimensional MR image data set from step S5 is required to determine the synovitis, this three-dimensional MR image data set can also be used for the automatic layer determination in S12. This has the advantage that it is not necessary to generate an additional three-dimensional overview image. The three-dimensional MR image data set from S5, however, has a higher resolution than a three-dimensional overview image, which advantageously produces better results in the automatic layer determination in S12.

For the layer determined in step S12, a two-dimensional T1-weighted MR image, from which T1 times are derived, is generated in step S13.

In the next step S14, the T1 times generated in step S3 are subtracted from the T1 times generated in step S13 and respective differences are produced.

From the differences which are analyzed according to predetermined evaluation parameters, which can be predetermined by the treating physician in step S15, an objective analysis of a proteoglycan proportion of the joint is generated in step S16. In other words, the proteoglycan proportion of the joint is determined by means of the T1 differences and the proteoglycan proportion thus generated is weighted through the predetermined evaluation parameters, resulting in a respectively reproducible analysis.

In step S21, the analyses regarding the synovitis and the proteoglycan proportion generated in step S10 and step S16 are combined, and from the results objective and reproducible evaluation parameters for the osteoarthritis are generated.

Finally, in step S22, these evaluation parameters are used to perform an objective and reproducible analysis of the osteoarthritis of the joint to be examined.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for automatically analyzing osteoarthritis of a joint, comprising the steps of:
    with a magnetic resonance imaging apparatus, generating a three-dimensional magnetic resonance image data set representing a three-dimensional volume of a predetermined region within a patient, said predetermined region containing at least a portion of a joint of the patient;
    in a processor, defining a plurality of different planar slices through said predetermined region and identifying a position for each different slice in said plurality of different slices by automatically identifying a predetermined anatomical orientation point for each of said different slices in said three-dimensional magnetic resonance image data set, and selecting the respective positions dependent on the respective predetermined anatomical orientation point;

in a processor, from said three-dimensional magnetic resonance image data set, generating, for each respective different slice in said plurality of different slices, a two-dimensional magnetic resonance image as a planar section through said three-dimensional volume;

in each respective different slice represented in the respective two-dimensional magnetic resonance images, automatically determining, in said processor, a thickness of a predetermined tissue therein and automatically analyzing a degree of inflammation in said joint dependent on the respective thicknesses, with respect to a reference, of the predetermined tissue in the respective different slices, and generating an analysis result representing said degree of inflammation;

in said processor, automatically designating one of said different slices in said joint dependent on a preset parameter representing the position of said one of said different slices;

injecting a contrast medium into the patient and thereafter generating a two-dimensional T1-weighted magnetic resonance image of said one of said different slices;

in said processor, automatically determining a proteoglycan proportion of said joint from said two-dimensional T1-weighted magnetic resonance image; and in said processor, automatically analyzing a degree of osteoarthritis in said joint, dependent on said degree of inflammation and said proteoglycan proportion, and emitting a representation of said degree of osteoarthritis at an output of said processor.

2. A method as claimed in claim 1 comprising designating the respective positions of each of said different layers in said plurality of different layers by automatically identifying a predetermined anatomical orientation point for each of said different layers in said three-dimensional magnetic resonance image data set, and calculating the respective positions dependent on the respective predetermined anatomical orientation points.

3. A method as claimed in claim 1 comprising automatically determining said thickness of said predetermined tissue in each of said different slices by automatically localizing said predetermined tissue in the respective two-dimensional magnetic resonance image for the respective slice, and automatically determining dimensions of the localized tissue in the respective slice.

4. A method as claimed in claim 1 comprising:
prior to injecting said patient with said contrast medium, generating a pre-injection two-dimensional T1-weighted magnetic resonance image of said on of said different slices;
in said processor, automatically generating a difference image from said pre-injection two-dimensional T1-weighted magnetic resonance image and said two-dimensional T1-weighted magnetic resonance image obtained after injecting said contrast medium; and
in said processor, automatically determining said proteoglycan proportion from said difference image.

5. A method as claimed in claim 4 comprising:
generating a three-dimensional magnetic resonance overview image of the patient and supplying said three-dimensional overview image to said processor as said three-dimensional magnetic resonance image data set; and
automatically determining said one of said different slices from said overview image for generating each of said pre-injection two-dimensional T1-weighted magnetic resonance image and said two-dimensional T1-weighted magnetic resonance image obtained after injecting said contrast medium.

6. A method as claimed in claim 1 comprising generating an overview magnetic resonance image only of the joint of the patient, and supplying said overview magnetic resonance image only of the joint to said processor as said two-dimensional magnetic resonance image data set.

7. An apparatus for automatically analyzing osteoarthritis of a joint, comprising:
a magnetic resonance data acquisition apparatus;
a control unit configured to operation said magnetic resonance data acquisition apparatus to acquire a three-dimensional magnetic resonance image data set representing a three-dimensional volume of a predetermined region within a patient, said predetermined region containing at least a portion of a joint of the patient;
a processor having an input via which a plurality of different planar slices through said predetermined region are defined, said processor being configured to identify a position for each slice in said plurality of different slices by automatically identifying a predetermined anatomical orientation point for each of said different slices in said three-dimensional magnetic resonance image data set, and selecting the respective positions dependent on the respective predetermined anatomical orientation point;
said processor, for each respective different slice in said plurality of different slices, being configured to generate, from said three-dimensional magnetic resonance image data set, a two-dimensional magnetic resonance image as a planar section through said three-dimensional volume;
said processor being configured to automatically determine, for each respective different slice in said plurality of slices represented in the respective two-dimensional magnetic resonance images, a thickness of a predetermined tissue therein and to automatically analyze a degree of inflammation in said joint dependent on the respective thicknesses, with respect to a reference, of the predetermined tissue in the respective different slice, and to generate an analysis result representing said degree of inflammation;
said processor being configured to automatically designate one of said different slices in said joint dependent on a preset parameter representing the position of said one of said different slices;
a magnetic resonance data acquisition unit;
a contrast agent injector;
a control unit configured to operate said magnetic resonance data acquisition unit and said contrast agent injector to inject a contrast medium into the patient and thereafter to generate a two-dimensional T1-weighted magnetic resonance image of said one of said different slices;
said processor being configured to automatically determine a proteoglycan proportion of said joint from said two-dimensional T1-weighted magnetic resonance image; and
said processor being configured to automatically analyze a degree of osteoarthritis in said joint, dependent on said degree of inflammation and said proteoglycan proportion, and to emit a representation of said degree of osteoarthritis at an output of said processor.

8. An apparatus as claimed in claim 7 wherein said processor is configured to automatically determine said thickness of said predetermined tissue in each of said different layers by automatically localizing said predetermined tissue in the respective two-dimensional magnetic resonance image for the respective layer, and to automatically determine dimensions of the localized tissue in the respective layer.

9. An apparatus as claimed in claim 7 wherein:
said control unit is configured to operate said magnetic resonance data acquisition unit, prior to injecting said patient with said contrast medium, to generate a pre-injection two-dimensional T1-weighted magnetic resonance image of said one of said different slices;
said processor is configured to automatically generate a difference image from said pre-injection two-dimensional T1-weighted magnetic resonance image and said two-dimensional T1-weighted magnetic resonance image obtained after injecting said contrast medium; and
said processor is configured to automatically determine said proteoglycan proportion from said difference image.

10. An apparatus as claimed in claim 9 wherein:
said control unit is configured to operate said magnetic resonance data acquisition unit to generate a three-dimensional magnetic resonance overview image of the patient, said three-dimensional overview image being supplied to said processor as said three-dimensional magnetic resonance image data set; and
said processor is configured to automatically determine said one of said different slices from said overview image for generating each of said pre-injection two-dimensional T1-weighted magnetic resonance image and said two-dimensional T1-weighted magnetic resonance image obtained after injecting said contrast medium.

11. An apparatus as claimed in claim 7 wherein said control unit is further configured to operate said magnetic resonance data acquisition unit to generate a three-dimensional magnetic resonance image only of the joint of the patient, and wherein said three-dimensional magnetic resonance image only of the joint is supplied to said processor as said three-dimensional magnetic resonance image data set.

* * * * *